United States Patent [19]
Dance

[11] Patent Number: 5,946,721
[45] Date of Patent: Sep. 7, 1999

[54] APPAREL FOR TRAINING EQUESTRIAN RIDING TECHNIQUES

[75] Inventor: Pamela G. Dance, Alpharetta, Ga.

[73] Assignee: Equilink, Inc., Alpharetta, Ga.

[21] Appl. No.: 09/036,395

[22] Filed: Mar. 6, 1998

[51] Int. Cl.⁶ ..................................................... A41B 1/00
[52] U.S. Cl. ............................ 2/69; 2/159; 2/171; 2/311; 36/83; 40/586
[58] Field of Search ............................... 2/69, 79, 93, 94, 2/85, 102, 108, 227, 228, 44, 45, 238, 171, 321, 172, 205, 311, 175.1, 195.1, 195.7, 244, 160, 159, 161.1, 161.5, 167, 169, 246, 214, 337, 338; 40/586; 36/83, 1, 109, 113–115, 131, 136, 137

[56] References Cited

U.S. PATENT DOCUMENTS

| | | |
|---|---|---|
| 3,381,307 | 5/1968 | Shingler ........................................ 2/94 |
| 3,790,963 | 2/1974 | Ealy ............................................... 2/79 |
| 4,365,354 | 12/1982 | Sullivan ....................................... 2/247 |
| 4,479,267 | 10/1984 | Radowsky, Jr. ........................... 2/44 X |
| 4,815,146 | 3/1989 | Theewis et al. .............................. 2/94 |
| 5,819,322 | 10/1998 | Dicker et al. ............................. 2/69 X |
| 5,836,016 | 11/1998 | Jacobs et al. ................................. 2/69 |

Primary Examiner—Gloria M. Hale
Attorney, Agent, or Firm—Kennedy, Davis & Kennedy, P.C.

[57] ABSTRACT

Horse riding apparel for training proper equestrian positioning of a rider for competition and casual riding, in which a hat, a shirt, and a pair of pants worn by the rider include signalling members for visually communicating the angulation and the posture of the rider while riding to an instructor so that the instructor may observe the rider and provide corrective guidance.

19 Claims, 3 Drawing Sheets

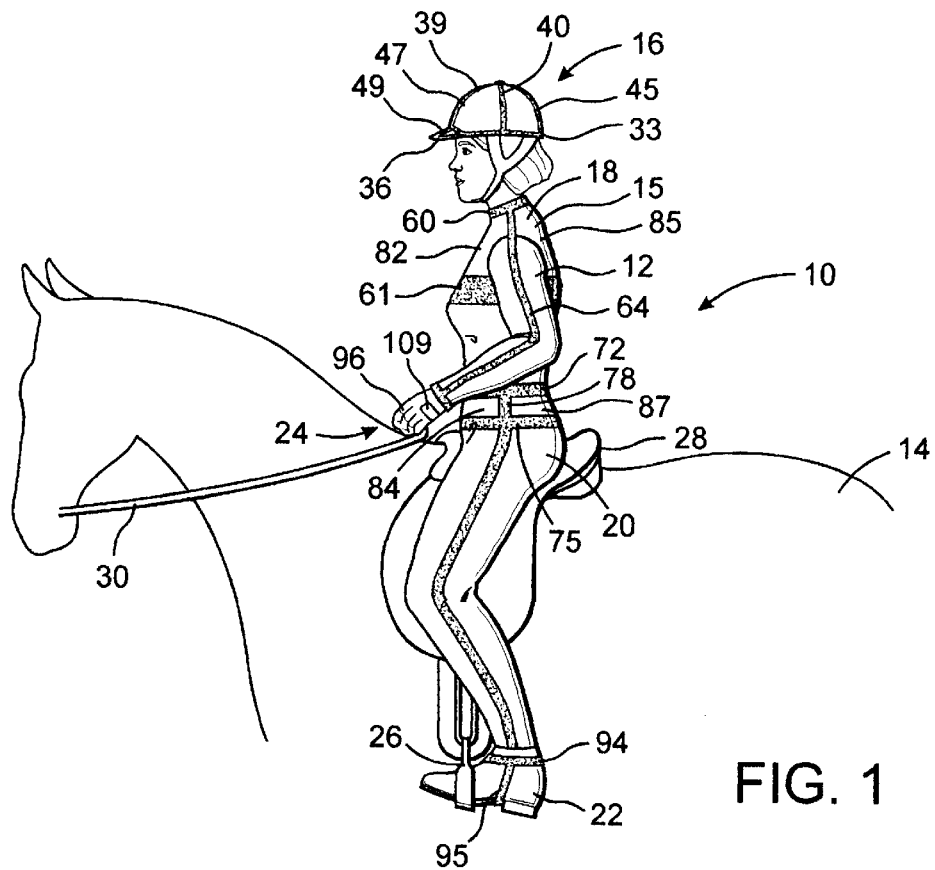
FIG. 1
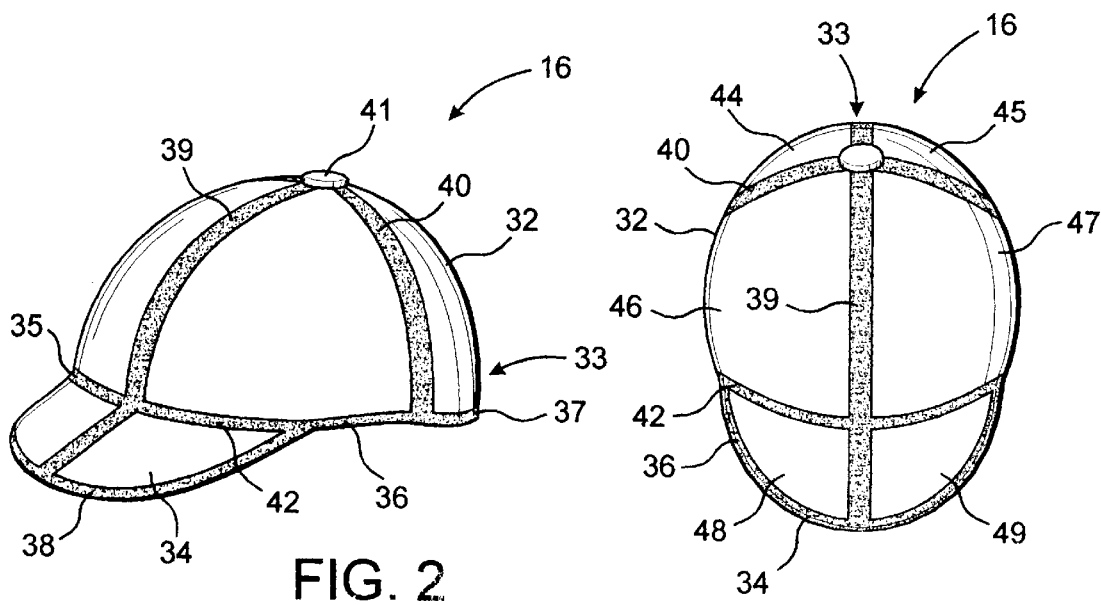
FIG. 2
FIG. 3

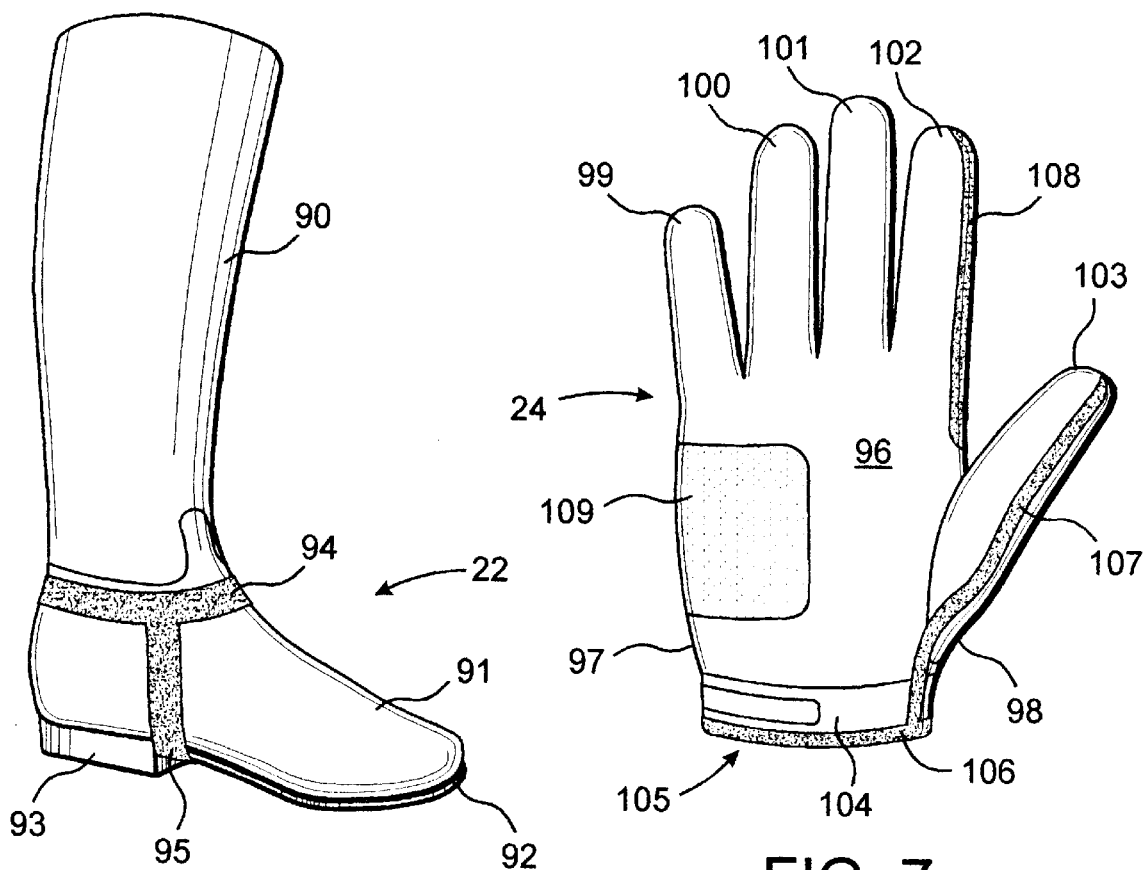
FIG. 6
FIG. 7
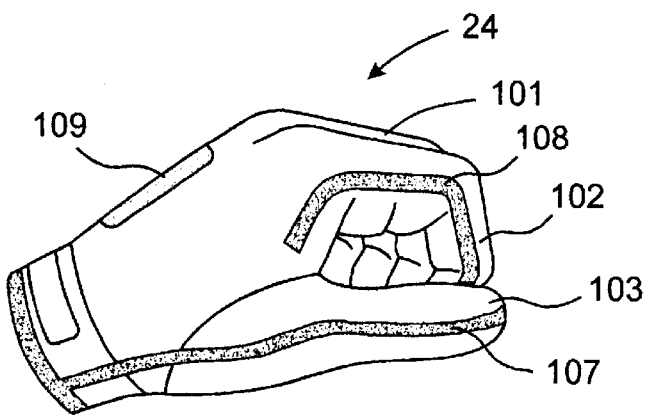
FIG. 8

APPAREL FOR TRAINING EQUESTRIAN RIDING TECHNIQUES

TECHNICAL FIELD

This invention relates generally to horse riding apparel. More particularly, the present invention relates to apparel worn by horse riders for visually communicating to an instructor the positioning of the rider's body for training equestrian riding techniques.

BACKGROUND OF THE INVENTION

In its simpler forms, apparel for riding horses has included clothing such as loincloths or tunics worn by ancient Greeks and Romans. In more complex forms, riding apparel has included armored suits having chain mail, breast plates, gauntlets and armets such as those worn in medieval times by knights for protection. Today, horse riding apparel is provided in many different styles particularly for sporting events. For instance, in racing horses, jockeys often wear brightly colored, loose-fitting outfits for visibly distinguishing themselves from other jockeys in a race. Such jockey outfits often include colors and numbers that correspond to colors and numbers provided on their horses such that both horse and jockey are distinguishable from the field of other jockeys and horses. In rodeo events, horse riders often wear rugged cowboy attire including a cowboy hat, button down shirt, jeans, chaps and cowboy boots. Uniforms are commonly worn by police personnel on horseback. Such uniforms may include a shirt of a blue or white color, black pants, black boots, a white helmet and a gun belt. Hand cuffs, guns, and other items attach to the gun belt. Still other styles of horse riding apparel are commonly worn for competition horse riding and jumping. These styles include black riding caps, red riding jackets, white or brown jodhpur pants, jodhpur boots, and riding gloves. Such existing riding apparel, however, is generally unsuitable for training proper horse riding techniques.

For example, in training for the sport of competitive horse riding a rider learns to guide a horse through a series of complex maneuvers by slight movements of the rider's hands, legs and weight. Judges of competitive horse riding award points to the rider for precisely moving and positioning the rider's body to maneuver the horse through a course of walking, trotting, circling, jumping, and the like. The development of proper riding techniques requires for competitive horse riding that the rider and the horse practice many hours of riding. An instructor typically facilitates the training of the rider and the horse. The instructor observes the precise body positioning of the rider as she or he rides the horse and provides corrective suggestions to the rider concerning the "angulation" and posture of a rider's body.

The term "angulation" refers to the angles of certain portions of the rider's body. Proper angulation is determined by the instructor visually assessing whether the rider's body is correctly positioned. For instance, an ankle angle between a rider's foot and shin should be bent at approximately 90 degrees. Other portions of the rider's body are held at approximately 135 degrees in relation to one another including a knee angle between a rider's calf and thigh, a hip angle between a rider's thigh and upper body, and an elbow angle between a rider's upper and lower arm. The angle of the rider's hands in relation to one another should be held at approximately 90 degrees with each of the rider's index fingers curled into a respective thumb at an approximately 90 degree angle. Of course, these angles may vary depending upon the style of riding, the size of the horse, and the size of the rider.

The term "posture" refers to the pitch, roll and yaw of the rider. The terms "pitch", "roll", and "yaw" refer to the positioning of the rider with respect to a three axis spatial orientation. Proper posture of the rider is determined by the instructor visually evaluating the pitch, roll and yaw of a rider's head, upper body, lower body, hands and feet individually and in relation to one another. The pitch of the rider's head refers to the forward or rearward pivotal movement of the head about a longitudinal axis at the juncture of the head and the upper body of the rider. The roll of the rider's head refers to the sideways pivotal movement of the head about a longitudinal axis at the juncture of the head and the upper body of the rider. The yaw of the rider's head refers to the rotational movement of the head about a vertical axis generally running through an upright centerline of the rider's body.

The pitch of the rider's upper body refers to the forward or rearward pivotal movement of the upper body about a longitudinal axis at the juncture of the upper body and the lower body of the rider. The roll of the rider's upper body refers to the sideways pivotal movement of the upper body about a longitudinal axis at the juncture of the upper body and the lower body of the rider. The yaw of the rider's upper body refers to the rotational movement of the upper body about a vertical axis generally running through an upright centerline of the rider's body.

The pitch of the rider's lower body refers to forward or rearward pivotal movement of the lower body about a longitudinal axis at the juncture of the lower body and the upper body of the rider. The roll of the rider's lower body refers to sideways pivotal movement of the lower body about a longitudinal axis at the juncture of the lower body and the upper body of the rider. The yaw of the rider's lower body refers to rotational movement of the lower body about a vertical axis generally running through an upright centerline of the rider's body.

The pitch of the rider's hands refers to the pivotal movement of each hand about a longitudinal axis at the juncture of the hand and the wrist of the rider. The "pitch" longitudinal axis is generally in the same plane as the fingers of the hand. The roll of the rider's hand refers to the rotational movement of the hand about a "roll" longitudinal axis extending generally in the same plane and centerline as the forearm to which the hand is connected. The yaw of the rider's hand refers to the sideways pivotal movement of the hand about a longitudinal axis transverse to the "pitch" longitudinal axis and the "roll" longitudinal axis.

The pitch of a rider's foot refers to the pivotal movement of the foot about a longitudinal axis extending generally through the rider's ankle. The "pitch" longitudinal axis of the foot is in a plane substantially parallel to the plane of the toes of the rider's foot. The roll of a rider's foot refers to the pivotal movement of the rider's foot about a "roll" longitudinal axis extending generally through the rider's ankle. The "roll" longitudinal axis is transverse to the "pitch" longitudinal axis and generally parallel to a centerline extending from the heel of the foot to the toes. The yaw of a rider's foot refers to the rotational movement of the foot about a longitudinal axis extending through a centerline substantially congruent with the lower leg of the rider.

Effective training of equestrian riding requires visual communication of a rider's angulation and posture to an instructor. Instructors who decipher quickly the body positioning of the rider are able to communicate corrective suggestions to the rider promptly for incorporation by the rider into his or her riding techniques at the time of the occurrence during the ride. Instructor's suggestions received after the fact must be considered with a recreation of the particular incident in hindsight by the rider in order for the rider to understand the corrective suggestion and incorporate the change into the rider's techniques. This subsequent recreation for correction is not entirely satisfactory.

Existing horse riding apparel is generally unsuitable for assisting instructors in accurately and quickly determining the proper angulation and posture of riders for communicating corrective feedback to riders during training rides. Rather than accelerating visual communication between the rider and the instructor, such existing apparel tends to hide the outline and positioning of a rider's body as the apparel is often loosely hung about the rider's body. Such apparel thereby impairs visual communication of the angulation and posture of the rider's body to the instructor. Also, the different pieces of clothing that comprise existing riding apparel neither cooperate nor align with one another to visually communicate to the instructor the angulation or posture of the rider's body parts in relation to one another. For example, in the above-described rodeo event attire, a cowboy hat merely covers the rider's head and shades the rider's eyes. Cowboy hats neither align nor cooperate with a button down shirt or blue jeans or chaps or boots for communicating proper angulation or posture of the rider's body. Other the heads and bodies of riders wearing such attire is difficult for an instructor to determine.

Moreover, existing horse riding apparel is designed to communicate messages to others that are unrelated to the body positioning of the rider. For instance, jockey outfits convey bright colors and numbers to observers to distinguish the jockeys from the field. Also, police uniforms are designed to communicate information about the officer's authority and serve to support police equipment such as guns and handcuffs. Thus, the visual communication of existing riding apparel distracts the observer from the evaluation of the angulation and posture of the rider's head and body.

Accordingly, there remains a need in the art for apparel that visually highlights to an instructor the angulation and positioning of a rider's head, upper body including arms and hands, lower body and feet. It is to the provision of such that the present invention is directed.

SUMMARY OF THE INVENTION

The present invention meets the above-described need in the art by providing a hat, a shirt, a pair of pants, a pair of gloves and a pair of boots, each of which is worn by a rider, with each having a plurality of signal members attached thereto for visually communicating the angulation and posture of the rider to an instructor for training proper equestrian riding techniques. The signal members define quadrants on the articles of apparel. The signal members and the quadrants facilitate the evaluation of the rider's positioning by instructors. In a second embodiment, the present invention comprises a K of straps for attachment to a clothing ensemble. The K of straps includes a first set of straps attached to a hat for defining at least four sections in said hat, a second set second embodiment, the present invention comprises a gridwork of straps for attachment to a clothing ensemble. The gridwork of straps includes a first set of straps attached to a hat for defining at least four sections in said hat, a second set of straps attached to a shirt for defining at least four sections in said shirt, and a third set of straps attached to a pair of pants for defining at least four sections in said pants. The first, second and third sets of straps substantially align and cooperate with one another to visually signal to a riding instructor whether a rider's body, head and limbs are properly aligned and cooperating with one another as to pitch, roll and yaw.

Objects, features and advantages of the present invention will become apparent upon reading the following detailed description of the disclosed embodiment of the present invention in conjunction with the appended drawings and claims.

BRIEF DESCRIPTION OF THE DRAWINGS

FIG. 1 is a side view of riding apparel, including a riding hat, a riding shirt, a pair of riding pants, a pair of riding boots, and a pair of gloves, according to the present invention being worn by a rider upon a horse.

FIG. 2 is a perspective view of the riding hat illustrated in FIG. 1.

FIG. 3 is an upper perspective view of the riding hat shown in FIG. 2.

FIG. 6 is a perspective view of a riding boot of the riding apparel illustrated in FIG. 1.

FIG. 7 is a side perspective view of the riding glove illustrated in FIG. 1.

FIG. 8 is a top view of the riding glove of FIG. 7 illustrating an index finger sleeve curled into a thumb sleeve of the glove as in a riding position.

DETAILED DESCRIPTION

Figure 4:
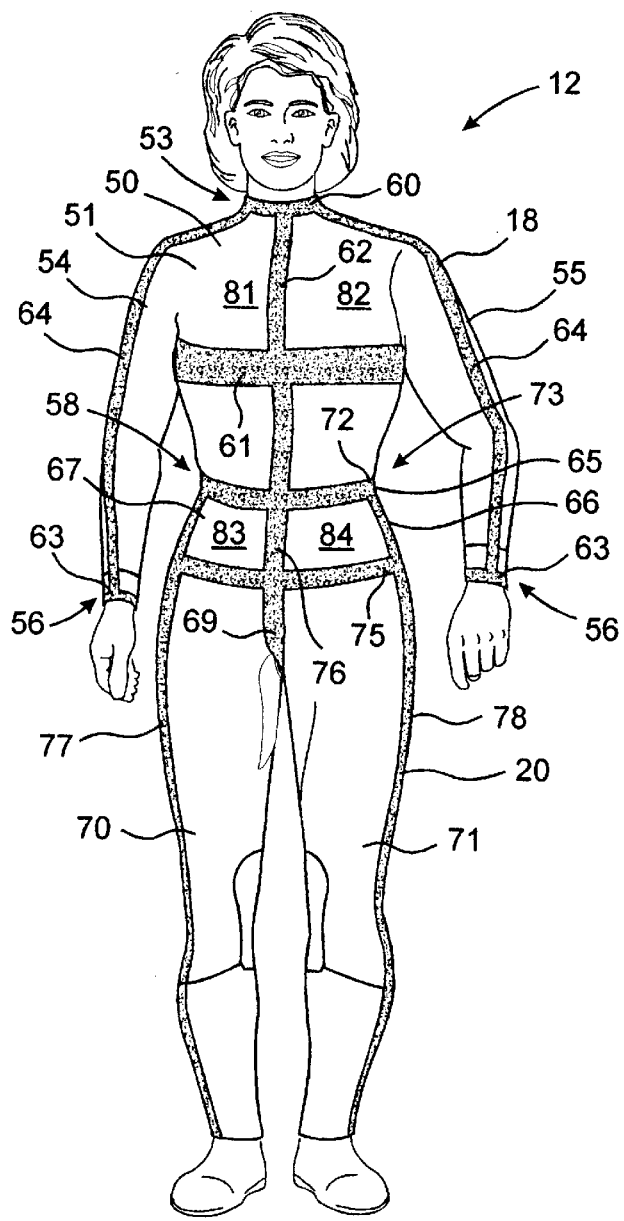
FIG. 4 is a front perspective view of a rider wearing the riding shirt and the pair of riding pants illustrated in FIG. 1.

Referring now in more detail to the drawings in which like numerals refer to like parts throughout the several views, FIG. 1 is a side view of riding apparel 10 according to the present invention being worn by a rider 12 upon a horse 14. The riding apparel 10 includes a hat 16, a shirt 18, a pair of pants 20, a pair of boots 22 and a pair of gloves 24 configured for visual indication to an instructor of the angulation of the rider 12. The rider 12 sits upright in a saddle 28 with the boots 22 in an opposing pair of stirrups 26 and with a pair of reins 30 in the rider's gloved hands 24. The structural features of each part of the riding apparel 10 are discussed separately below. FIG. 1 is referred to together with the other drawings to describe the different parts of the riding apparel 10.

FIG. 2 is a perspective view of the riding hat 16 illustrated in FIG. 1. A housing 32 and a visor 34 define the riding hat 16. The housing 32 and the visor 34 are preferably comprised of a metal or rigid plastic material for protecting the rider's head and are covered by a fabric material such as felt or velvet. The visor 34 attaches to a forward edge of the housing at a juncture 35. The visor 34 extends outwardly from the housing 32. The housing 32 and the visor 34 are preferably of the same color, for purposes discussed below.

A plurality of signal members attach to the housing 32 and the visor 34. The signal members are preferably narrow ribbons of a fabric material attached to the housing 32 and the visor 34 by sewing, bonding with an adhesive, or other fixative mechanism. The signal members are preferably of a color or colors that contrast with the color of the housing 32 and with the color of the visor 34.

A first signal member 36 of the plurality of signal members attaches to the housing 32 and the visor 34 along a lower peripheral edge 37 of the housing and an outer edge 38 of the visor. A second signal member 39 attaches to the housing 32 and the visor 34. The second signal member 39 extends from a rearward edge 33 on the lower peripheral edge 37 of the housing 32 to the outer edge 38 of the visor 34. The second signal member 39 is preferably disposed in a plane defined by a longitudinal axis that bisects the hat 16 into left and right sides.

A third signal member 40 attaches to the housing 32 along a plane substantially transverse to the second signal member 39. The third signal member 40 extends between two opposing points on the lower peripheral edge 37 of the housing 32. The third signal member 40 is disposed intermediate of the forward edge 35 and the rearward edge 33 of the housing 32. Preferably, the third signal member 40 is disposed medial the forward edge 35 and the rearward edge 33 to thereby divide the housing 32 into forward and rearward portions. A button 41 attaches to the housing 32 at the point where the second signal member 39 and the third signal member 40 intersect. A fourth signal member 42 attaches to the riding hat 16 and extends along the juncture 35 of the housing 32 and the visor 34.

FIG. 3 is an upper perspective view of the riding hat 16 shown in FIG. 2. The second and third signal members 39 and 40 segment the housing 32 of the hat 16 into four quadrants 44, 45, 46, and 47. These four quadrants 44, 45, 46 and 47 define opposing forward right and left quadrants and opposing rearward right and left quadrants. The second signal member 39 segments the visor 34 into opposing right and left panels 48 and 49.

FIG. 4 is a front perspective view of a rider 12 wearing the riding shirt 18 and the pair of riding pants 20 illustrated in FIG. 1. The shirt 18 has a main body section 50 for covering the upper torso of a person's body. The main body section 50 includes a front side 51, a rear side 52 (shown in FIG. 5), and a neck opening 53. A pair of sleeves 54 and 55 extend from the main body section 50 for receiving a person's arms therethrough. Each of the sleeves 54 and 55 has a wrist opening 56 for receiving a person's wrist therethrough. The main body section 50 has a waist opening located generally at 58 for receiving a person's waist therethrough. The main body section 50 and the pair of sleeves 54 and 55 are comprised of a flexible fabric material to which other fabric materials can be sewn, bonded with an adhesive, or otherwise affixed thereto. The main body section 50 and the pair of sleeves 54 and 55 are preferably of the same color.

A plurality of signal members attach to the main body section 50 and the pair of sleeves 54 and 55. The signal members are preferably flexible fabric material strips that attach to the main body section 50 and the pair of sleeves 54 and 55 by sewing, bonding with an adhesive, or other fixative mechanism. The signal members are preferably of a color or colors that contrast with the color of the main body section 50 and with the color of the pair of sleeves 54 and 55.

A collar signal member 60 attaches to the main body section 50 and extends around the neck opening 53. A chest signal member 61 attaches to the main body section 50 in a plane substantially parallel to the collar signal member 60. The chest signal member 61 extends around the front side 51 and the rear side 52 of the main body section 50. A front signal member 62 attaches to the front side 51 of the main body section 50. The front signal member 62 extends from the collar signal member 60 to the waist opening 58 in a plane substantially transverse to the collar signal member. The front signal member 62 defines two opposing panels 81 and 82 in the front side 51 of the shirt 18.

A wrist signal member 63 attaches to a distal end of each of the sleeves 54 and 55 and extends around each of the wrist openings 56. A side signal member 64 attaches to each of the sleeves 54 and 55. Each of the side signal members 64 extends from the collar signal member 60 to the wrist signal member 63.

A pair of pants 20 includes a waist section 65 that defines a waist opening 73 for receiving the rider's waist therethrough. A hip section 66 of the pants 20 includes a front side 67 and a rear side 68 (shown in FIG. 5) and a crotch 69. The hip section 66 extends from the waist section 65. A right leg section 70 depends from the hip section 66 for covering a right leg of a person wearing the pants 20. A left leg section 71 depends from the hip section 66 for covering a left leg of a person wearing the pants 20. The waist section 65, the hip section 66, the right leg section 70 and the left leg section 71 are comprised of a flexible fabric material to which other fabric materials can be sewn, bonded with an adhesive, or otherwise affixed thereto, and are preferably of the same color.

A plurality of signal members attach to the waist section 65, the hip section 66, the right leg section 70 and the left leg section 71. The signal members are preferably flexible fabric material strips that attach to the waist section 65, the hip section 66, the right leg section 70 and the left leg section 71 by sewing, bonding with an adhesive, or other fixative mechanism. The signal members are preferably of a color or colors that contrast with the color of the waist section 65, the hip section 66, the right leg section 70 and the left leg section 71.

A waist signal member 72 attaches to the waist section 65 and extends around the waist opening 73 in a generally longitudinal plane. A hip signal member 75 attaches to the hip section 66. The hip signal member 75 extends around the hip section 66 in a plane substantially parallel to the waist signal member 72. A front lower body signal member 76 attaches to the front side 67 of the hip section 66. The front lower body signal member 76 extends from the waist signal member 72 to the crotch 69 along an axis substantially transverse to the longitudinal plane of the waist signal member 72. The front lower body signal member 76 defines two opposing panels 83 and 84 in the front side 67 of the pants 20.

A right leg signal member 77 attaches to the right leg section 70. The right leg signal member 77 extends the length of the right leg section 70 from the waist signal member 72 along an axis substantially transverse to the longitudinal plane of the waist signal member. A left leg signal member 78 attaches to the left leg section 71. The left leg signal member 78 extends the length of the left leg section 71 from the waist signal member 72 along an axis substantially transverse to the longitudinal plane of the waist signal member.

Figure 5:
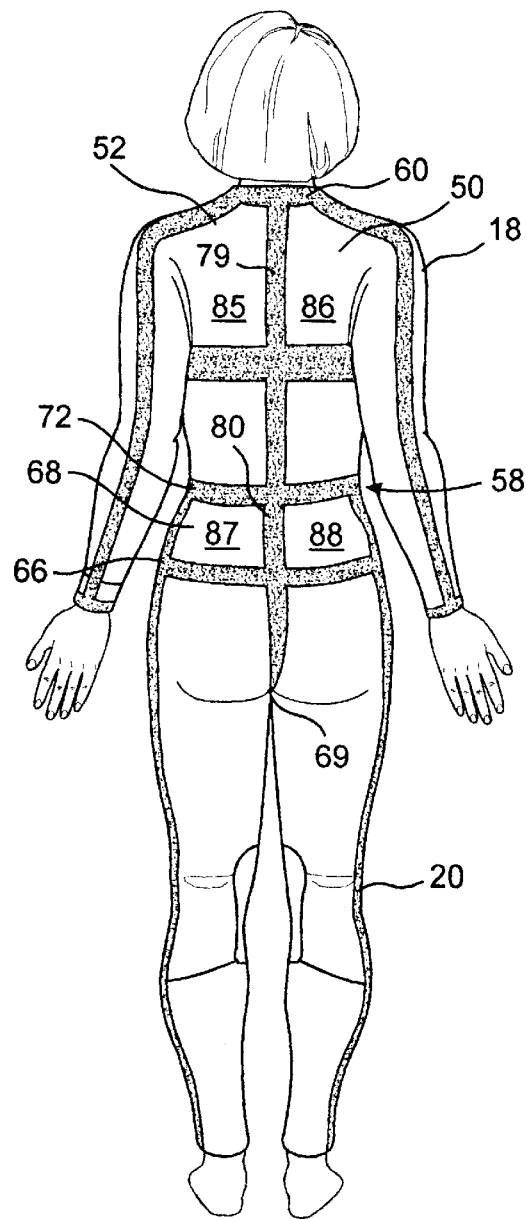
FIG. 5 is a rear perspective view of the riding shirt and the pair of riding pants illustrated in FIG. 1.

FIG. 5 is a rear perspective view of the riding shirt 18 and the riding pants 20 illustrated in FIG. 1. A rear signal member 79 attaches to the rear side 52 of the main body section 50 of the shirt 18. The rear signal member 79 extends from the collar signal member 60 to the waist opening 58. The rear signal member 79 intersects the collar signal member 60 opposite the front signal member 62. The rear signal member 79 defines two opposing panels 85 and 86 in the rear side 52 of the shirt 18. The rear signal member 79 and the front signal member lie in substantially the same longitudinal plane.

A rear lower body signal member 80 attaches to the rear side 68 of the hip section 66 of the pants 20. The rear lower body signal member 80 extends from the waist signal member 72 to the crotch 69. The rear lower body signal member 80 defines two opposing panels 87 and 88 in the rear side 68 of the pants 20. The rear lower body signal member 80 and the front lower body signal member 76 lie in substantially the same longitudinal plane.

FIG. 6 is a perspective view of a riding boot 22 of the riding apparel illustrated in FIG. 1. The boot 22 has an upper portion 90, a lower portion 91 and a sole 92. A heel 93 attaches to the sole 92. An ankle signal member 94 and a heel signal member 95 detachably attach to the lower portion 91 of the boot 22. The ankle signal member 94 and the heel signal member 95 are preferably flexible fabric material strips. The distal ends of the heel signal member 95 connect to the ankle signal member 94 at opposing points on the ankle signal member. The ankle signal member 94 detachably fastens to itself by connection means such as a snap, or hook and loop fasteners, or button and loop fasteners. The ankle signal member 94 extends around the lower portion 91 of the boot in a longitudinal plane. The heel signal member 95 extends around the sole 92 of the boot 22 in a longitudinal plane that is substantially transverse to the longitudinal plane of the ankle signal member 94. The signal members 94 and 95 of the boots 22 are preferably of a color that contrasts with the color of the boots.

FIG. 7 is a side perspective view of the riding glove 24 illustrated in FIG. 1. The glove 24 includes a backhand section 96 for covering a back section of a hand. A forehand section (unshown) opposes the backhand section 96. A lateral exterior edge 97 and a lateral interior edge 98 join the forehand section to the backhand section 96. Finger sleeves 99, 100, 101 and 102 and a thumb sleeve 103 depend from the backhand section 96 and the forehand section. A wristband 104 attaches to the forehand section and backhand section 96 and defines an opening 105 for receiving a hand therethrough.

The glove 24 includes a plurality of glove signal members. The glove signal members are preferably flexible fabric material strips that attach to the wristband 104, the lateral interior edge 98, the thumb sleeve 103 and the index finger sleeve 102 by sewing, bonding with an adhesive, or other fixative mechanism. The first glove signal member 106 attaches to the wristband 104. The first glove signal member 106 preferably extends around the opening 105 in a longitudinal plane. A second glove signal member 107 attaches to the lateral interior edge 98 and to a portion of the thumb sleeve 103. The second glove signal member 107 extends along an axis substantially transverse to the plane of the first glove signal member 106.

A third glove signal member 108 attaches to the finger sleeve 102 adjacent the thumb sleeve 103. The third glove signal member 108 preferably extends the length of the finger sleeve 102. A fourth glove signal member 109 is preferably comprised of a heavy fabric sufficiently durable to withstand wear caused by contact with the reins 30 as illustrated in FIG. 1. The fourth glove signal member 109 attaches to the lateral exterior edge 97 and a portion of the forehand section (unshown) and a portion of the backhand section 96.

FIG. 8 is a top view of the riding glove 24 of FIG. 7 illustrating the index finger sleeve 102 curled into a thumb sleeve 103 of the glove as in a riding position.

The signal members 106, 107, 108 and 109 of the gloves 24 are preferably of a color that contrasts with the color of the forehand and backhand sections 96 of the gloves. The fourth glove signal member 109 is preferably of a color that contrasts with the forehand and backhand sections 96 and with the signal members 106, 107 and 108.

When the rider is properly positioned, it is preferred that the third signal member 40 of the riding hat 16, an upper portion of the side signal members 64, an upper portion of the leg signal members 77 and 78, and the heel signal members 95 align with one another in substantially the same longitudinal plane. Preferably, the second signal member 39 of the riding hat 16, the front and rear signal members 62 and 79, and the front and rear lower body signal members 76 and 80 align with one another in the same longitudinal plane.

The operation of the riding apparel 10 is understood with reference to FIGS. 1–8. Beginning with FIG. 1, the riding apparel 10 visually communicates the angulation and posture of the rider to an instructor viewing the riding apparel as in FIG. 1. The third signal member 40 of the hat 16, the side signal member 64 of the shirt 18, the left leg signal member 78 of the pants 20 and the heel signal member 95 of the boot 22 substantially align with one another thereby indicating to an instructor that the pitch and the yaw of the rider's head, the pitch and the yaw of the upper body, the pitch and the yaw of the lower body, and the pitch and the yaw of the feet are proper, individually and in relation to one another. The contrasting colors of the signal members and the quadrants of the apparel facilitate the visual communication of the angulation of the rider to the instructor.

The riding apparel 10, shown in FIG. 1, also visually signals the instructor that the roll and the yaw of the head, the roll and the yaw of the upper body, the yaw of the lower body and the yaw of the left foot are proper, individually and in relation to one another because only the left side of the rider 12 is visible. The right quadrants 44 and 46 of the housing 32 and the right panel 48 of the visor 34, shown in FIGS. 2 and 3, are hidden from the instructor's view. This indicates that the roll and the yaw of the rider's head is proper. The right front and rear shirt panels 81 and 86, shown in FIGS. 4 and 5, are hidden from the instructor's view. This indicates that the roll and the yaw of the rider's upper body is proper. The right front and rear lower body panels 83 and 88, shown in FIGS. 4 and 5, are hidden from the instructor's view. This indicates that the yaw of the rider's lower body is proper.

If the quadrant 44 is visible to the instructor viewing the rider 12 (as in FIG. 1), the riding apparel 10 thereby signals the instructor that the yaw of the head is improper as the head is turned counterclockwise. If the quadrant 46 is visible to the instructor viewing the rider 12 (as in FIG. 1), the riding apparel 10 thereby signals the instructor that the yaw of the head is improper as the head is turned clockwise. If both quadrants 44 and 46 are visible to the instructor viewing the rider 12 (as in FIG. 1), the riding apparel 10 thereby signals the instructor that the roll of the head is improper as the head is rolled too far toward the instructor.

If the right front shirt panel 81 is visible to the instructor viewing the rider 12 (as in FIG. 1), the riding apparel 10 thereby signals the instructor that the rider's upper body has assumed an improper counterclockwise yaw. If the right rear shirt panel 86 is visible to the instructor, the riding apparel 10 thereby signals the instructor that the rider's upper body has assumed an improper clockwise yaw. If the right front lower body panel 83 is visible to the instructor, the riding apparel 10 thereby signals the instructor that the rider's lower body has assumed an improper counterclockwise yaw. If the right rear lower body panel 88 is visible to the instructor, the riding apparel 10 thereby signals the instructor that the rider's lower body has assumed an improper clockwise yaw.

Also, in FIG. 1, the first signal member 36 of the riding hat 16 aligns in a substantially parallel plane with the collar signal member 60 and the chest signal member 61 of the shirt 18, the waist signal member 72 and the hip signal member 75 of the pants 20, and the ankle signal member 94 of the boot 22, thereby indicating to the instructor that the pitch and the roll of the rider's head is proper. The collar signal member 60 and the chest signal member 61 of the shirt 18 align in a substantially parallel plane with the first signal member 36 of the riding hat 16, the waist signal member 72 and the hip signal member 75 of the pants 20, and the ankle signal member 94 of the boot 22 thereby indicating to the instructor that the pitch and the roll of the rider's upper body is proper. The waist signal member 72 and the hip signal member 75 of the pants 20 align in a substantially parallel plane with the first signal member 36 of the riding hat 16, the collar signal member 60 and the chest signal member 61 of the shirt 18, and the ankle signal member 94 of the boot 22 thereby indicating to the instructor that the pitch and the roll of the rider's lower body is proper. The ankle signal member 94 of the boot 22 aligns in a substantially parallel plane with the first signal member 36 of the riding hat 16, the collar signal member 60 and the chest signal member 61 of the shirt 18, and the waist signal member 72 and the hip signal member 75 of the pants 20, thereby indicating to the instructor that the pitch and the roll of the rider's foot is proper. Visual exposure of the fourth glove signal member 109 to the instructor, as in FIG. 1, communicates to the instructor that the roll of the rider's hand is proper.

As best described through FIGS. 3 and 5, the riding apparel 10 visually communicates the rider's angulation and posture to an instructor viewing the rider from a rear perspective. The second signal member 39 of the hat 16, the rear signal member 79 of the shirt 18, and the rear lower body signal member 80 of the pants 20 align in substantially the same plane to signal the instructor that the roll and the yaw of the rider's head, upper body and lower body are proper, individually and in relation to one another. As viewed from this rear perspective, the quadrants 46 and 47 of the hat (shown in FIGS. 2 and 3), the front shirt panels 81 and 82 (shown in FIG. 4), and the front lower body panels 83 and 84 (shown in FIG. 4) are hidden from the instructor's line of sight. This indicates that the pitch and the yaw of the head, the pitch and the yaw of the upper body, and the yaw of the lower body are proper, individually and in relation to one another.

If the quadrant 46 is visible to the instructor, the riding apparel 10 thereby signals the instructor that the rider's head has assumed an improper clockwise yaw. If the quadrant 47 is visible to the instructor, the riding apparel 10 thereby signals the instructor that the rider's head has assumed an improper counterclockwise yaw. If the quadrants 46 and 47 of the hat 16 are visible simultaneously to the instructor, the riding apparel 10 thereby signals the instructor that the head is improperly pitched rearward.

From a front perspective as best shown in FIGS. 3 and 4, the second signal member 39 of the hat 16, the front signal member 62 of the shirt 18 and the front lower body signal member 76 of the pants 20 align in substantially the same plane to indicate to the instructor that the roll and yaw of the head, the upper body and the lower body are proper individually and in relation to one another. The quadrants 44 and 45 of the hat (shown in FIGS. 2 and 3), the rear shirt panels 85 and 86 (shown in FIG. 5), and the rear lower body panels 87 and 88 (shown in FIG. 5) are hidden from the instructor's line of sight. This indicates that the pitch and the yaw of the head, the pitch and the yaw of the upper body, and the yaw of the lower body are proper, individually and in relation to one another.

If the quadrant 44 is visible to the instructor, the riding apparel 10 thereby signals the instructor that the rider's head has assumed an improper counterclockwise yaw. If the quadrant 45 is visible to the instructor, the riding apparel 10 thereby signals the instructor that the rider's head has assumed an improper clockwise yaw. If the quadrants 44 and 45 of the hat 16 are visible simultaneously to the instructor, the riding apparel 10 thereby signals the instructor that the head is improperly pitched forward.

From a right side perspective, if the quadrant 45 is visible to the instructor viewing the rider 12 from a perspective opposite that in FIG. 1, the riding apparel 10 thereby signals the instructor that the yaw of the head is improper as the head is turned counterclockwise. If the quadrant 47 is visible to the instructor, the riding apparel 10 thereby signals the instructor that the yaw of the head is improper as the head is turned clockwise. If both quadrants 45 and 47 are visible to the instructor viewing the rider 12, the riding apparel 10 thereby signals the instructor that the roll of the head is improper as the head is rolled too far toward the instructor.

If the left front lower body panel 84 is visible to the instructor viewing the rider 12 from a perspective opposite that of FIG. 1, the riding apparel 10 thereby signals the instructor that the rider's lower body has assumed an improper clockwise yaw. If the left rear lower body panel 87 is visible to the instructor, the riding apparel 10 thereby signals the instructor that the rider's lower body has assumed an improper counterclockwise yaw.

Turning to FIGS. 7 and 8, the operation of the gloves 24 enables a rider to observe whether or not the hands are in proper position for holding the reins of a horse. The rider's line of sight to the gloves 24 during a ride is essentially the same as that illustrated in FIG. 8. Visual exposure of a small portion of the fourth glove signal member 109 to the rider signals the rider that the roll of the hands is proper. If more or less than a small portion of the fourth glove signal member 109 is visible to the rider, the glove 24 thereby signals the rider that the hand has assumed an improper roll position. The second glove signal member 107 aligns at an approximate 90 degree angle to the first glove signal member 106 to visually signal the rider that the yaw of the hand is proper. The third glove signal member 108 curls into the second glove signal member at an approximate 90 degree angle to signal the rider that the fingers are curled properly into the thumb sleeve 103 for proper holding of the reins 30.

In an alternate embodiment, the present invention provides a gridwork of straps that attach to a clothing ensemble worn by a rider. The gridwork includes several sets of straps. The clothing ensemble includes the riding hat 16, the riding shirt 18, the riding pants 20, the riding boots 22, and the riding gloves 24. As seen in FIGS. 1–3, a first set of straps includes the signal members 39 and 40 that attach to the riding hat 16. The first set of straps 39 and 40 define four sections 44, 45, 46 and 47 in the hat 16. The signal members 36 and 42 are preferably included in the first set of straps.

As seen in FIGS. 1, 4, and 5, a second set of straps includes the signal members 61, 62 and 79 that attach to the riding shirt 18. The second set of straps 61, 62 and 79 define the sections 81, 82, 85 and 86 in the riding shirt 16. The signal members 60 and 64 are preferably included in the second set of straps.

A third set of straps includes the signal members 75, 76, and 80 that attach to the riding pants 20. The third set of straps 75, 76, and 80 define the sections 83, 84, 87, and 88 in the pants 20. The signal members 72 and 77 are preferably included in the third set of straps.

As seen in FIGS. 7 and 8, a fourth set of straps includes the signal members 106, 107 and 108 that attach to the gloves 24. As seen in FIGS. 1 and 6, a fifth set of straps includes the signal members 94 and 95 that attach to the boots 22.

The gridwork of straps is preferably comprised of flexible fabric strips of material. The gridwork may be permanently attached to the clothing ensemble by sewing, bonding with an adhesive or other fixative mechanism. The gridwork may also be detachably connected to the clothing ensemble by means of matingly engageable fastening devices such as hook and loop fasteners, snap buttons, button and loop closures, clips, and other such mateable fasteners. The gridwork may also be comprised of elastic bands or paint. One skilled in the art should readily appreciate the number of types and combinations of material that could be used to embody and affix such sets of straps to the clothing ensemble.

When attached to the clothing ensemble, the gridwork of straps operates in the same manner as previously described with regard to the pluralities of signal members attached to the riding hat 16, the shirt 18, the pair of pants 20, the pair of boots 22 and the pair of gloves 24, for signalling to an observing instructor the angulation of the rider for learning equestrian riding techniques.

It thus is seen that a new riding apparel for teaching proper equestrian riding is now provided that overcomes problems long associated with those of prior art. It should be understood however that many modifications, additions and deletions may be made thereto without departure from the spirit and scope of the invention as set forth in the following claims.

What is claimed is:

1. A riding hat for use in instructing proper pitch, roll, and yaw of the head of a rider for centered equestrian riding purposes, comprising:

a housing defining a cavity for being received upon a head of a rider of a horse and having a lower periphery;

a visor projecting outwardly from a forward edge on said lower periphery of said housing along a longitudinal axis and having an outer edge, said housing and said visor being of a first color;

a first signal member extending along at least a portion of said lower periphery of said housing and said outer edge of said visor;

a second signal member attached to said housing and said visor and extending in a plane substantially parallel to said longitudinal axis from a rearward edge on said lower periphery of said housing opposite said visor to said outer edge of said visor; and a third signal member attached to said housing and extending in a plane substantially transverse to said longitudinal axis between a pair of opposing points on said lower periphery of said housing,
   said third signal member disposed intermediate said forward and rearward edges;
   said first, second and third signal members being of a second color contrasting with said first color,
   whereby the contrast between the second color of the first, second and third signal members and the first color of the housing and the visor visually signals a riding instructor as to whether the head of the rider is properly oriented while the rider is riding a horse.

2. The riding hat of claim 1 wherein said third signal member is disposed medial said forward and rearward edges of said lower periphery of said housing.

3. The riding hat of claim 1 wherein said second signal member is in a plane aligned with said longitudinal axis.

4. The riding hat of claim 1 wherein said second and third signal members define two opposing rearward quadrants and two opposing forward quadrants on said housing, whereby visual exposure of the quadrants in a riding instructor's line of sight signals the instructor as to whether the rider's head is properly positioned.

5. The riding hat of claim 1 wherein said second signal member defines opposing panels in said visor, whereby visual exposure of the panels in a riding instructor's line of sight signals the instructor as to whether the rider's head is properly positioned.

6. A shirt for use in instructing proper upper body posture for centered equestrian riding purposes, wherein the shirt has a main body section for covering an upper torso of a person's body, said main body section having a front side, a rear side, a neck opening for receiving a person's neck therethrough, a pair of sleeves extending from said main body section for receiving a person's arms therethrough, each of said pair of sleeves having a wrist opening for receiving a person's wrist therethrough, and a waist opening for receiving a person's waist therethrough, the improvement comprising:

a collar signal member attached to said main body section and extending around said neck opening;

a chest signal member attached to said main body section and extending around an upper portion of said main body section in a plane substantially parallel to said collar signal member;

a front signal member attached to said front side of said main body section and extending from said collar signal member to said waist opening in a plane substantially transverse to said collar signal member;

a rear signal member attached to said rear side of said main body section and extending from said collar signal member to said waist opening in a plane substantially transverse to said collar signal member;

a pair of wrist signal members, each extending around a respective one of said wrist openings;

a pair of side signal members, each attached to a respective one of said pair of sleeves and extending from said collar signal member to said wrist signal member on the respective sleeve, said main body section and sleeves being of a first color, and said collar, chest, front, rear, and side signal members being of a second color contrasting with said first color, whereby the contrast between the second color of the signal members and the first color of the main body section and the sleeves visually signals a riding instructor as to whether the upper body of the rider is properly oriented for centered equestrian riding.

7. The shirt of claim 6 wherein the side signal member defines an approximate 45 degree angle when the rider's arm is bent at the elbow for proper arm positioning.

8. The shirt of claim 6 wherein said front signal member is disposed on said front side medial said sleeves and defines two opposing front panels of said front side of said main body section of said shirt, whereby visual exposure of one or both of the front panels to a riding instructor's line of sight signals the instructor as to whether the rider's upper body is in proper yaw position.

9. The shirt of claim 6 wherein said rear signal member is disposed on said rear side medial said sleeves and defines two opposing rear panels of said rear side of said main body section of said shirt, whereby visual exposure of one or both of the rear panels to a riding instructor's line of sight signals the instructor as to whether the rider's upper body is in proper yaw position.

10. A pair of pants for use in instructing proper lower body posture for centered equestrian riding purposes, in which the pants have a waist section defining an opening for receiving a person's waist therethrough, a hip section having a front side, a rear side, and a crotch, said hip section extending from said waist section, a right leg section joined to said hip section for covering a right leg of a person wearing the pants, a left leg section joined to said hip section for covering a left leg of the person, the improvement comprising:

- a waist signal member attached to said waist section and extending around said waist opening in a generally longitudinal plane;
- a hip signal member attached to said hip section and extending around said hip section in a plane substantially parallel to said waist signal member;
- a front lower body signal member attached to said front side of said hip section and extending from said waist signal member to said crotch along an axis substantially transverse to said longitudinal plane of said waist signal member;
- a rear lower body signal member attached to said rear side of said hip section and extending from said waist signal member to said crotch along an axis substantially transverse to said longitudinal plane of said waist signal member;
- a right leg signal member attached to said right leg section and extending the length of said right leg section along an axis substantially transverse to said longitudinal plane of said waist signal member;
- a left leg signal member attached to said left leg section and extending the length of said left leg section along an axis substantially transverse to said longitudinal plane of said waist signal member; and
- said waist section, hip section, and right and left leg sections reflect a first color, and said hip, front lower body, rear lower body, right leg, and left leg signal members reflect a second color contrasting with said first color,
- whereby the contrast between the second color of the signal members against the first color of the waist section, hip section, and right and left leg sections visually signals a riding instructor as to whether the lower body of the rider is properly oriented while the rider is riding a horse.

11. The pants of claim 10 wherein said front and rear lower body signal members and said right and left leg signal members define four quadrants between said waist signal member and said hip signal member, whereby visual exposure of the quadrants in a riding instructor's line of sight signals the instructor as to whether the rider's lower body is in proper yaw position.

12. A gridwork of straps for attachment to a clothing ensemble for visually signalling variance in body, limb and head positioning of a rider for evaluating and instructing centered horse riding techniques, the gridwork comprising:

- a first set of straps attached to a hat for defining at least four sections in said hat;
- a second set of straps attached to a shirt for defining at least four sections in said shirt; and
- a third set of straps attached to a pair of pants for defining at least four sections in said pants,
- whereby said first, second and third sets of straps substantially align and cooperate with one another to visually signal to a riding instructor whether a rider's body, head and limbs are properly aligned and cooperating with one another.

13. The gridwork of claim 12 wherein each set of straps includes a front strap and a rear strap substantially aligned in a first plane, and a right strap and a left strap substantially aligned in a second plane transverse to the first plane, whereby the four sections of the hat, the four sections of the shirt, and the four sections of the pants are substantially aligned with one another.

14. The gridwork of claim 13 further comprising a fourth set of straps attached to a pair of gloves for alignment with said left strap and said right strap of said second set of straps.

15. The gridwork of claim 13 further comprising a fifth set of straps attached to a pair of boots for alignment with said left strap and said right strap of said third set of straps.

16. The gridwork of claim 12 wherein the sets of straps are of a first color and the sections are of a second color contrasting to the first color.

17. A pair of gloves for use in instructing proper hand positioning of a horse rider, each glove comprising a forehand section for covering a fore section of a hand, a backhand section joined to said forehand section along a lateral exterior edge and a lateral interior edge, a wristband joined to said forehand and backhand sections and defining an opening for receiving a hand therethrough, four finger sleeves extending from a portion of the forehand and backhand sections opposite the wristband, and a thumb sleeve extending from the forehand and backhand sections adjacent the four finger sleeves, the improvement comprising:

- a first glove signal member attached to said wristband and extending along a portion of said wristband in a plane;
- a second glove signal member attached to said lateral interior edge and to a portion of said thumb sleeve, said second glove signal member extending on an axis substantially transverse to said plane of said wrist signal member;
- a third glove signal member attached to and extending along a portion of a finger sleeve adjacent said thumb sleeve;
- a fourth glove signal member attached to said lateral exterior edge and a portion of said forehand section and said backhand section opposite said thumb sleeve,
- said wristband, said forehand and backhand sections, said finger sleeves, and said thumb sleeve being of a first color, and
- said first, second, third and fourth glove signal members being of a second color contrasting with said first color,
- whereby the glove signal members visually indicate to an instructor and to a rider whether a rider's hands are in proper riding position.

18. The gloves of claim 17 wherein said fourth glove signal member has a third color contrasting with the first color of each glove and the second color of the first, second and third glove signal members.

19. The gloves of claim 17 wherein said second glove signal member substantially separates said forehand section from said backhand section such that visual exposure of one or both of the sections in a rider's line of sight signals the instructor as to whether the rider's hands are in proper position.

* * * * *